(12) United States Patent
Dobos

(10) Patent No.: US 6,512,158 B1
(45) Date of Patent: Jan. 28, 2003

(54) MEDICAL PROTECTIVE WRAP

(75) Inventor: John A. Dobos, E. Amherst, NY (US)

(73) Assignee: Medwrap Corporation, Amherst, NY (US)

( * ) Notice: Subject to any disclaimer, the term of this patent is extended or adjusted under 35 U.S.C. 154(b) by 0 days.

(21) Appl. No.: 09/478,756

(22) Filed: Jan. 6, 2000

Related U.S. Application Data

(63) Continuation of application No. PCT/US98/14553, filed on Jul. 14, 1998.
(60) Provisional application No. 60/052,473, filed on Jul. 14, 1997.

(51) Int. Cl.$^7$ ................................................ A61F 13/00
(52) U.S. Cl. ............................................ 602/41; 602/3
(58) Field of Search .................... 128/878, 879, 128/882; 602/3, 5, 13, 60, 63, 41–47, 79

(56) References Cited

U.S. PATENT DOCUMENTS

| | | | |
|---|---|---|---|
| 3,037,507 A | 6/1962 | Melges | 128/292 |
| 4,253,451 A | 3/1981 | Solomon | 128/132 |
| 4,294,240 A * | 10/1981 | Thill | 602/21 |
| 4,482,414 A * | 11/1984 | Schonberger | 156/79 |
| 4,516,572 A * | 5/1985 | Schlein | 602/3 |
| 4,523,586 A | 6/1985 | Couri | 128/82 |
| 4,788,972 A * | 12/1988 | DeBusk | 602/5 |
| 4,829,992 A * | 5/1989 | Cilladi et al. | 602/6 |
| 4,911,151 A | 3/1990 | Rankin et al. | 128/82 |
| 5,035,687 A * | 7/1991 | Sandbank | 604/180 |
| 5,052,387 A * | 10/1991 | Natali | 607/108 |
| 5,063,919 A | 11/1991 | Silverberg | 128/82 |
| 5,088,483 A * | 2/1992 | Heinecke | 602/46 |
| 5,395,302 A | 3/1995 | Botha et al. | 602/3 |
| 5,630,430 A | 5/1997 | Shultz et al. | 128/888 |
| 5,823,977 A | 10/1998 | Dalyea | 602/3 |

FOREIGN PATENT DOCUMENTS

JP 5925857 * 2/1984

* cited by examiner

Primary Examiner—Michael A. Brown
Assistant Examiner—Lalita M Hamilton
(74) Attorney, Agent, or Firm—Howard M. Ellis

(57) ABSTRACT

Medical protective wraps made of a liquid impermeable, stretchable polymeric material which provide a watertight seal and barrier to protect wounds from contamination due to dirt, microbes or infiltration of water during bathing while not constricting blood flow to the healing tissue. The protective wraps comprise a liquid impermeable stretchable polymeric sheet of a sufficient length to wrap around the body part at least once. Positioned along opposing peripheral edges of the polymeric sheet are sealing cuffs having reduced stretchability relative to the sheet. Also, there are first and second terminal edges running transverse to the longitudinal axis of the peripheral edges. A fastener is attached to the first terminal edge which secures the sheet to the body and the second terminal is fastened to the sheet after at least one wrapping of the sheet around the body part.

22 Claims, 4 Drawing Sheets

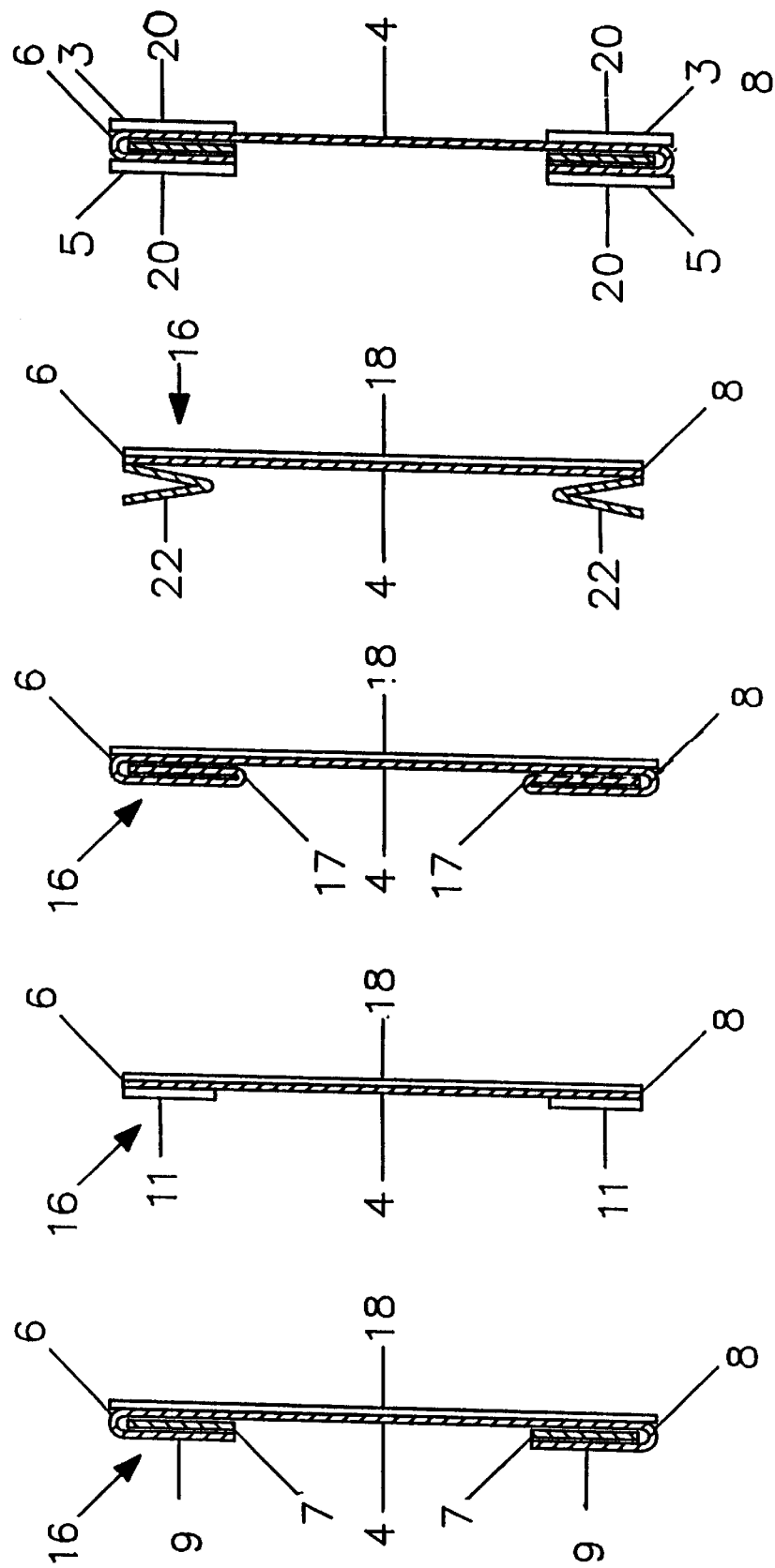

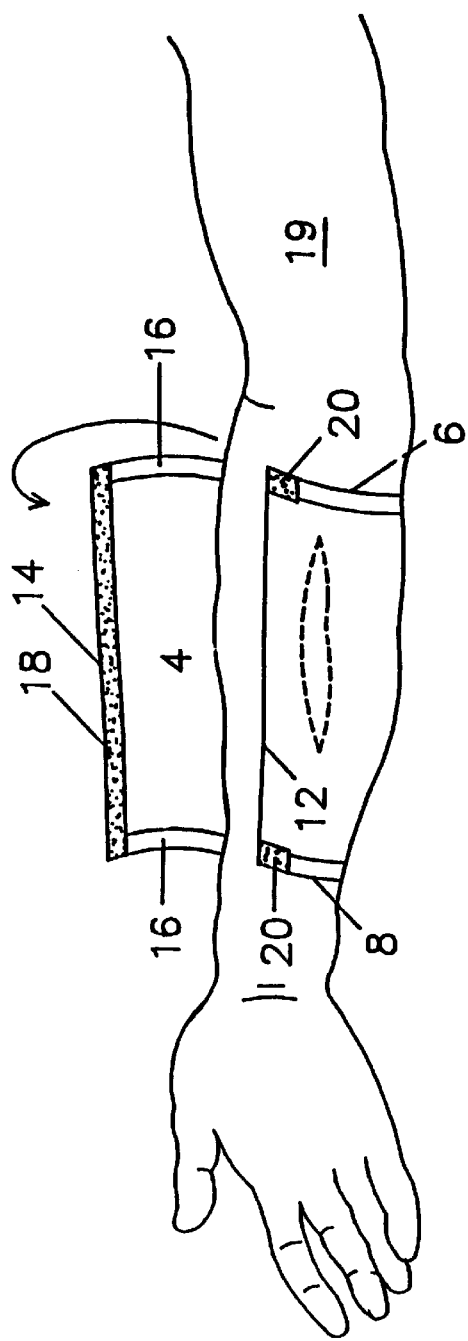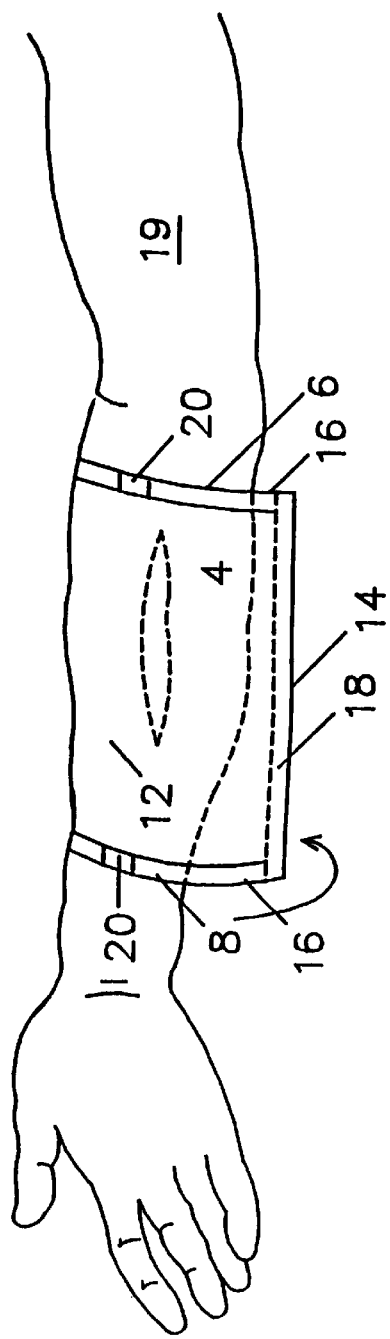

MEDICAL PROTECTIVE WRAP

CROSS REFERENCE TO RELATED APPLICATION

This application is filed under 35 U.S.C. 111(a) and claims the benefit of Copending International Application filed under the Patent Cooperation Treaty as PCT/US98/14553 on Jul. 14 1998, which claims priority under U.S. Provisional Application No. 60/052,473, filed on Jul. 14, 1997.

TECHNICAL FIELD

The present invention relates generally to medical protective wraps and in particular to medical protective wraps made of liquid impermeable, flexible, polymeric material having watertight sealing cuffs which in combination provide a watertight barrier to protect wounds or surgical incisions from contamination due to dirt, microbes or infiltration of water during bathing without applying constricting pressure on tissue near the wound.

BACKGROUND OF THE INVENTION

After surgery or a serious injury a major concern of most patients is the ability to return to normal routines which include bathing or showering. This often presents a problem because the wound must be maintained in a sterile condition without contamination from water or dirt. In the past, many watertight dressings have been developed but these waterproof protective covers may also restrict movement of the involved body part. This restriction of movement may hinder progress of a rehabilitation program especially if waterproof protection is required for therapeutic sessions in a whirlpool.

Typical of the most common forms of protection from exposure to external water and dirt for an injured limb include bag-type structures. Some patents representative of this type of structure are as follows: U.S. Pat. No. 4,523,586 to Couri issued Jun. 18, 1985; U.S. Pat. No. 5,152,282 to Elphick et al issued Oct. 6, 1992; U.S. Pat. No. 5,395,302 to Botha et al issued on Mar. 7, 1995; and U.S. Pat. No. 5,720,712 to Joy et al issued Feb. 24, 1998. However, this type of covering presents several disadvantages. For instance, if the wounded area involves an arm then placement of a bag-type structure over the arm eliminates the use of the encased hand for participating in normal routines. In the case of a leg, the foot is virtually immobilized in the bag-type structure. Moreover, movement is difficult and dangerous because of the possibility of further injury due to the potential risk of slippage on the bag structure.

Additionally, several of the protective coverings currently available use elastic closures or some type of constriction on the peripheral edges of the wrap or bag to maintain a watertight seal. Examples of this type of closure are shown in U.S. Pat. No. 2,911,974 to Spence issued on Nov. 12, 1959 and Botha et al supra. It is believed that restrictive elastic closures may be counter-productive to healing because the additional pressure on the tissue beneath the elastic closure can cause a reduction of blood flow to the area thereby slowing the healing process.

Other types of protective wraps utilize a strip of adhesive tape or a tacky strip on the peripheral edges of the protective covering for protecting an injury or incision, such as that disclosed in U.S. Pat. No 1,707,515 to Evans issued on May 29, 1926. However, this type of adhesive strip can introduce a high level of discomfort to the patient when the cover or wrap is removed especially if the tape adheres to a patient's body hair. Furthermore, there may be seal leakage at particular sections that are stressed during body movement allowing water infiltration to the wound site.

Some protective covers may present difficulties in the application process, such as shown in Elphick et al and Botha et al supra. As a result, a patient cannot place and adjust the protective covering without the help of a second hand or another individual. Several wraps, currently available, require two hands to adjust and secure the wrap. As such, help may be required from a second party if the injury is on an arm or hand, especially if the covering needs to be held with one hand and tightened by another hand.

In the past, most protective coverings for wounds have included some type of absorbent material, with the thought that wicking away of bodily fluids aids in healing. But, there is considerable literature to indicate that a drying environment may slow healing time and also increase scar tissue formation due to forcing the migration of epidermal cells under a scab which has formed in a dry environment.

Accordingly, there is a need for protective wraps which are constructed of flexible, liquid impermeable materials, self-applying with one hand and providing a watertight barrier for bathing without causing restriction of blood flow to the site of injury over extended periods of use.

SUMMARY OF INVENTION

The present invention meets the aforementioned needs by providing improved, disposable, liquid impermeable flexible medical protective wraps for wounds that can be self-applied and adjusted by the user and can be worn for extended periods without restricting blood flow to the injury site.

For purposes of this invention, the terms and expressions below, appearing in the specifications and claims, are intended to have the following meanings"

"Wound" as used herein means a surgical incision, laceration or any other injury that needs to be protected by the present invention.

A primary object of the present invention is to provide a medical protective wrap for protecting a wound on a body part which comprises:

a) a sheet of liquid impermeable, stretchable, flexible polymeric film of a sufficient length to wrap around the body part at least once;

b) a first and second peripheral edge on opposing ends of the sheet;

c) a sealing cuff extending along the first and second peripheral edge, the sealing cuff having reduced stretchability relative to the sheet;

d) a first and second terminal edge on the sheet running transverse to the longitudinal axis of the first and second peripheral edge; and e) at least one means for fastening on the first terminal edge and second terminal edge.

The means for fastening on the first terminal edge may be on both sides of the sheet thereby providing a means for fastening on the top side of the first terminal edge which may adhere to the body part. On the bottom side of the first terminal edge is a means for fastening which may adhere to the sheet at the position where the sheet has made one complete wrap around the body part. The means for fastening on the second terminal edge is secured to the sheet thereby providing a watertight seal along the second terminal edge.

A primary advantage of the present invention is that it provides a water-tight seal without elastic closures thereby avoiding reduced blood flow to the wound area. Additionally, the protective wrap is secured to the body part with a minimum of adhesive sites and does not rely exclusively on adhesive bonding directly to the body part for forming a water-tight barrier.

In one embodiment the sheet of liquid impermeable, stretchable, flexible polymeric film may be treated with an antimicrobial agent. This treatment may include impregnation of the polymeric film prior to forming the medical wrap of the present invention.

In another embodiment of the present invention it may be desirable to employ a low moisture vapor permeable, liquid impermeable polymeric film for fabrication of the medical wrap sheet. The low moisture vapor permeable, water impermeable polymeric film maintains a moist environment which is believed to be capable of accelerating wound healing but also allows for some evaporation of any excess water in the exudate from a wound thereby helps to prevent blisters from forming under the medical wrap.

Another advantage is that the protective wrap is non-reusable thereby eliminating concerns of disinfecting the medical wrap between applications.

The medical protective wrap can be applied to an injury or wound on a body part, the medical protective wrap comprising a liquid impermeable stretchable polymeric sheet of a sufficient length to wrap around the body part at least once, having sealing cuffs with reduced stretchability positioned along opposing first and second peripheral edges of the sheet, having first and second terminal edges running transverse to the longitudinal axis of the first and second peripheral edges, having a means of fastening to the body part on the top side of the first terminal edge and means for fastening to the sheet on the bottom side of the first terminal edge and the second terminal edge, the method comprising the steps of:

a) applying to the body part the means for fastening on the top side of the first terminal edge of the sheet;

b) stretching and wrapping the sheet snugly around the body part including the wound site at least once thereby adhering the sheet to the means for fastening on the bottom side of the first terminal edge wherein the body part is in contact with the sheet and the sealing cuffs having a flush fit with the tissue of the body providing a sufficiently watertight fit to prevent infiltration of liquid to the wound site without constriction of same; and c) fastening the second terminal edge to the sheet thereby providing a sufficiently watertight fit to prevent infiltration of liquid to the wound site on the second terminal edge.

BRIEF DESCRIPTION OF DRAWINGS

The present invention will now be described by way of example with reference to the accompanying drawings in which:

FIGS. 2, 3, 4 and 5 are enlarged cross-sectional views as taken at line A—A of FIG. 1 showing several different embodiments of sealing cuffs.

FIG. 6 is an enlarged cross-sectional view as taken at line B—B of FIG. 1 showing means for fastening the medical protective wraps of the invention.

FIGS. 7 and 8 show the application of the medical protective wrap of FIG. 1.

DESCRIPTION OF THE PREFERRED EMBODIMENTS

Figure 1:
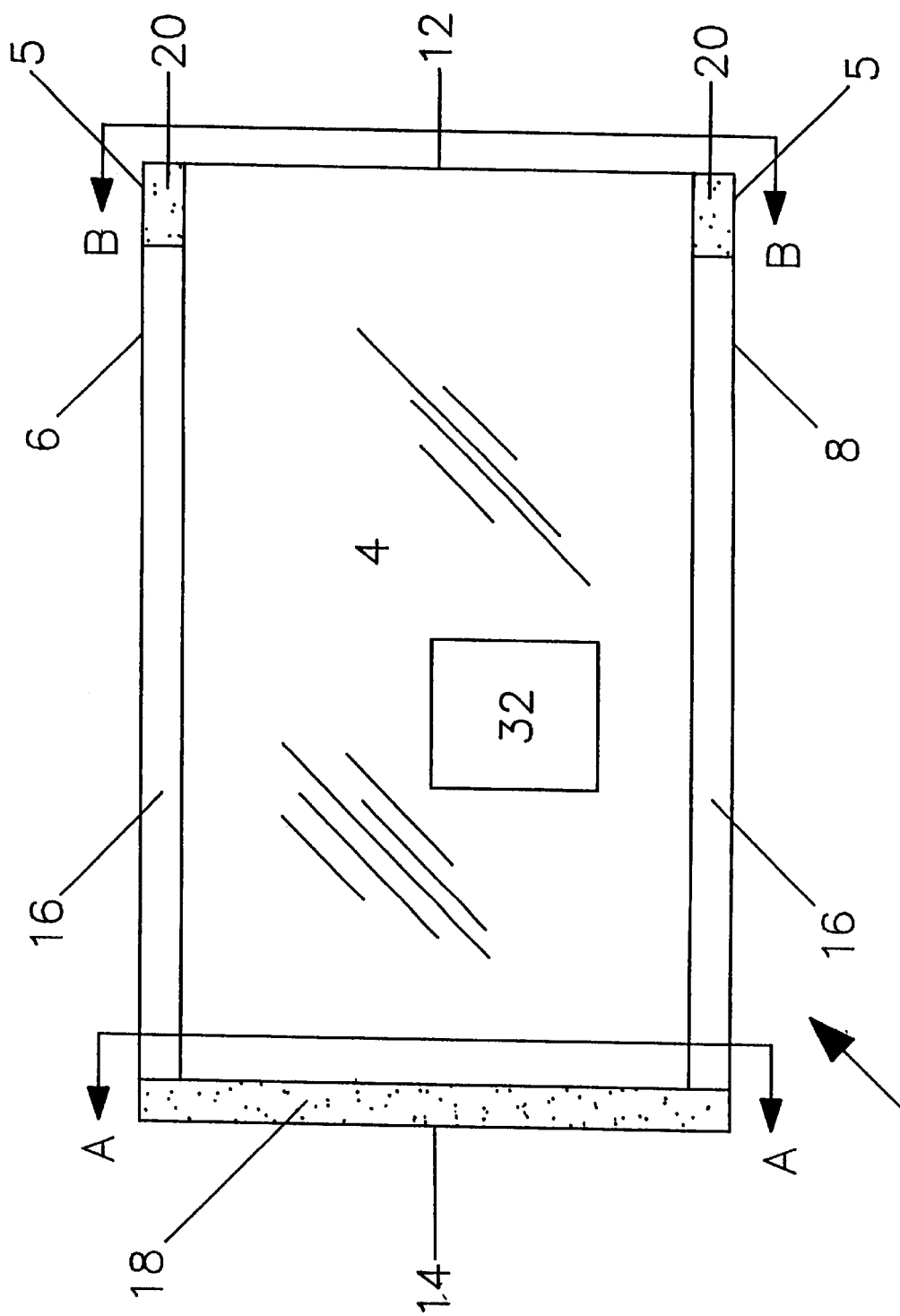
FIG. 1 shows a top plan view of one embodiment of the medical protective wrap.

The preferred embodiments of the present invention and their advantages are best understood by referring to FIGS. 1–10 of the drawings, like numerals being used for like and corresponding parts of the various drawings.

It is understood that the thickness of the layers of materials and other dimensions in the drawings have been greatly exaggerated for purposes of illustration. Further, directions, such as top and bottom refer to the location of the various members in the drawing and, in general, also to their positions relative to the patient. "Top" refer to a location adjacent to the patient's skin, while "bottom" refers to a location remote from the patient's skin.

A preferred embodiment of medical protective wrap 10 made according to the invention is illustrated in FIG. 1. The medical protective wrap 10 comprises a sheet 4 which is fabricated from a liquid impermeable, non-absorbent, and stretchable polymeric film. The polymeric film can be sterilized to provide a sterile environment when used by patients. The dimensions of sheet 4 are determined by the particular end use, that being a patient's size, the dimensions of a body part being dressed, or the unique configuration of the body part such as a shoulder or heel. It should be noted the term body part includes but is not limited to limbs, hands and feet, torso of the body and any joint such as shoulder, elbow, ankle and knee. Thus understood, sheet 4 is wide enough to cover the wound site and preferably a sufficient length so as to extend more than once completely around the body part. The specific polymeric film should be stretchable and flexible so that the protective wrap can conform snugly to the size and shape of the body part but also provide ease of movement of the covered body part. The polymer film used in the fabrication of this medical protective wrap may include flexible plastics that possess moderate-to-high degrees of crystallinity and a wide range of $T_{melting}$ and $T_{glass}$ values. These flexible plastics have moderate-to-high moduli (15,000–350,000 N/cm$^2$), tensile strengths (1500–7000 N/cm$^2$), and ultimate elongation (20–800%). Polyethylene is a preferred flexible plastic having a tensile strength of about 2500 N/cm$^2$, a modulus of about 20,000 N/cm$^2$ and an ultimate elongation of 500%. Preferably, the thickness of the polymeric film can range from about 1 to about 10 mil, and more preferably in the range of about 2 to about 4 mil. An especially preferred polyethylene is a film product offered by Atlantis Plastic, namely, NP-1100 which is a general purpose low-density polyethylene film having a modulus of 15,000 to 18,000 N/cm$^2$, tensile strength of about 1800 N/cm$^2$, and an ultimate elongation of about 200%. This polymeric film can be embossed in different patterns: such as taffeta (52 squares per inch), pebble and fine diamond (110 squares per inch) with a minimum thickness of about 1 mil. An embossed pattern has been found to be effective in not only offering the stretchability for a secure and snug fit of the protective wrap but also enhances the ease of applying the wrap because of reduced twisting and clinging of the polyethylene film to itself due to static attractions. Other flexible and stretchable plastics that may be utilized can include but not limited to polypropylene, poly(vinyl chloride), polystyrene, polyurethane, poly (hexamethylene adipamide), polysiloxane and any coated non-woven fabrics.

In accordance with this invention sheet 4 may also be fabricated of a polymeric film impregnated with an antimicrobially effective amount of an antimicrobial agent to effectively inhibit the growth of bacteria on either side of the sheet, that being near the wound or the outer surface of the medical wrap. The antimicrobial agent may be present in the polymeric film in an amount ranging from about 0.1 to about 25% by weight of the antimicrobial agent. Any antimicrobial agent that inhibits the growth of Gram-positive and Gram-negative organisms may be used. In a preferred embodiment, 2,4,4'-trichloro-2'-hydroxydiphenyl ether, available from Microban Products Co., Huntersville, N.C. is incorporated into the polymer of choice prior to fabrication of the medical protective wrap.

It is further envisioned by the inventor of the present invention that the liquid impermeable, stretchable, flexible polymeric film of sheet 4 may be a polymeric film which has the above characteristics but also has low moisture vapor permeability. By low moisture vapor permeability is meant a moisture vapor permeability of about 300 grams per square meter per 24 hours at 40° C. to about 1200 grams per square meter per 24 hours at 40° C. and 80% relative humidity difference. This inventor has discovered that treating wounds with a dressing that is liquid impermeable and moisture vapor permeable allows the wound site to remain moist to enhance healing but also allows moisture vapor from wound exudate to evaporate through sheet 4 when wrapped around wound site. Materials that have a low moisture vapor permeability may include polyurethane, polyolefin films, such as polyethylene, polybutadiene; polyolefin copolymers such as ethylene-vinyl acetate copolymers; polyisobutylene and the like.

Moisture vapor permeability referred to herein and in the claims refers to moisture vapor permeability determined in accordance with the following method:

1. Take a sample of the polymeric material containing no perforations and cut a 1.25 inch diameter sample,
2. fill a container with water,
3. place the sample on the container so that a 1 inch diameter is tested,
4. weigh the assembly,
5. place the assembly in an oven set at 40° C., for 48 hours at 20% relative humidity,
6. remove the assembly and weigh,
7. calculate the water loss in grams per meter squared per 24 hours at 80% relative humidity differential at 40° C.

On opposing ends of sheet 4 are first and second peripheral edge 6 and 8, respectively. These edges define the placement of a sealing cuff 16 which provides a watertight seal when sheet 4 is wrapped around a body part. The sealing cuff 16 with reduced stretchability, relative to the stretchability of sheet 4 thereby forms a reinforced sealing cuff which circumvents the body part above and below the site of injury without causing constriction of blood vessels in the tissue beneath the sealing cuff. The sealing cuff 16 as illustrated in FIG. 1 extends along the length of sheet 4 on opposing peripheral edges 6 and 8 and can preferably have widths in the range from about 1.5 to about 6.5 cm, and more preferably from 2.5 to about 4.5 cm.

FIGS. 2, 3, 4, and 5 show various different embodiments of the sealing cuff 16 wherein each embodiment has reduced stretchability relative to the flexibility and stretchability of the sheet 4. FIG. 2 provides a sealing cuff 16 wherein flap 9, which is merely an extension of main sheet 4 that has been folded along first and second peripheral edges 6 and 8 and sealed with a double faced adhesive strip 7. A wide variety of different double faced adhesive strip are known in the art and may be employed in practicing this invention. The double faced adhesive strip may be any liquid proof liner strip covered with medical grade adhesive, such as an acrylic pressure-sensitive adhesive. The sealing cuff 16 is subject to considerable stress but by reinforcing the cuff with the inclusion of strip 7, additional strength is added. The sealing cuff 16 in the process of winding around the body part causes a flush fit with the tissue of the body part without constriction of the tissue and also draws the entire sheet 4 flush to the body part thereby causing sheet 4 to adhere to the wound or injury.

FIG. 3 shows a single faced adhesive strip 11 attached directly to sheet 4 along the first and second peripheral edges 6 and 8. The tacky side of the single adhesive side of strip 11 will adhere to sheet 4 leaving the un-tacky side to come in contact with the body part. To accomplish a flush fit of sealing cuff 16 with the tissue of the body part the single faced adhesive strip must cause a reduced stretchability in the sealing cuff relative to the stretchability of sheet 4.

FIG. 4 shows the sealing cuff 16 comprising at least one folding of the main sheet 4. The first fold is at the first and second peripheral edges 6 and 8 and another fold at 17. This folding of sheet 4 onto itself causes a reduced stretchability of sealing cuff 16 relative to the stretchability of a single layer of sheet 4. The double folding shown in FIG. 4 or a plurality of folds forms the sealing cuff 16 and provides additional strength to withstand any stress during winding of the wrap. Also, the double folding provides an adequate surface area for a watertight seal. The folds forming the sealing cuff may be spot welded with heat, inclusion of an adhesive strip, or heat sealed to maintain folding.

FIG. 5 reveals the sealing cuff 16 with an attached v-shaped strip 22 which is secured to sheet 4 with either adhesive or heat welding along the first and second peripheral edges 6 and 8. This embodiment provides a reduced stretchability in the sealing cuff 16 relative to the sheet 4 and the trough shaped grove provides an additional water barrier during bathing. The apex of the v-shaped strip 22 extends inwardly towards the interior of the wrap and each other.

The four different embodiments of sealing cuff 16 are merely representative of the options available for the sealing cuff and may be oriented in the opposite direction from that shown in the figures. Furthermore, all embodiments of the sealing cuff 16 have little or no puckering or gathering of the sealing cuff or along sheet 4 which would introduce the effect of an elastic closure. The lack of gathering reduces constriction of tissue beneath the sealing cuff.

In FIG. 1, positioned on sheet 4 and running transverse to the longitudinal axis of the first and second peripheral edge 6 and 8 are first and second terminal edge 12 and 14, respectively. The first and second terminal edge 12 and 14 support means for fastening wrap 10 around the protected body part. In this embodiment, on opposite ends of the first terminal edge 12 having a the bottom side 3 (shown in FIG. 6) and top side 5 on sheet 4, and affixed to sealing cuff 16, are means for fastening 20. These means for fastening may include four (4) corner tabs of hypo-allergenic adhesive tape, such as shown in FIG. 6, or a strip of hypo-allergenic adhesive tape which folds over first terminal edge 12 thereby providing a source of tacky contact on both sides of first terminal edge 12. The fasteners 20 on first terminal edge 12 allow fixation to the body part with the hypo-allergenic tape and prevent movement or rotation of sheet 4 on the limb during the stretching and winding of sheet 4. Fasteners 20 also permit sheet 4 to be securely fixed to the body part to enable the application of the wrap to be performed by a single hand, if necessary. The adhesive materials employed may be any of the known medical or hyper-allergenic adhesives employed in securing the dressing to the skin of the body part. Such known adhesives include the rubber-based, acrylic, vinyl ether and hydrocolloid pressure sensitive adhesives. The adhesive may be applied to provide a layer of at least 0.5 mil thick, and preferably between 0.8 and 1 mil thick.

The adhesive may be protected from contamination prior to use by suitable removable covers and the adhesive tabs or movable covers may extend beyond terminal edge 12. Additionally, the removable covers can be color coded to aid in the proper alignment of the protective wrap during plication by the user.

After the fasteners 20 on the top side 5 of the first terminal edge adhere to the body part the remaining portion of sheet 4 is free and can envelop the body part including the site of the wound or incision.

With continued stretching and wrapping of sheet 4 around the circumference of the body part, sheet 4 will make contact with bottom side 3 of fasteners 20 and thereby provide a second fixing point for sheet 4.

A watertight closure is facilitated by means for fastening 18 on the second terminal edge 14 of sheet 4. The means for fastening 18 may include a waterproof strip of adhesive tape that extends the entire length of second terminal edge 14, on one side, from first peripheral edge 6 to second peripheral edge 8. A wide variety of waterproof adhesive materials may be used in the present invention and are well known in the art. The means for fastening 18 provides for an infinite number of positions of closure and thereby accommodates body parts of varying sizes.

FIGS. 7 and 8 illustrate steps of application of the medical protective wrap 10 which is shown in FIG. 1, wherein sheet 4 is initially attached to limb 19 with top side 5 of first terminal edge 12 with means of fastening 20. Sheet 4 is then grasped and stretched snugly around the limb once to the point where the bottom side 3 of the corner tabs of hypoallergenic tape fastener 20 on the first terminal edge 12 engage and adhere to sheet 4. This specific placement of the hypo-allergenic tape on the corners of first terminal edge 12 has several purposes; firstly, the placement of the corner adhesive tabs provides a point of adherence to the limb 19 to prevent slippage of the wrap thereby preventing reduced tension in the sealing cuff causing the wrap to rotate on the limb 19 and secondly, when attempting to apply the protective cover on one's arm it can be easily manipulated without the presence of another person to secure the protective wrap. Additionally, the open area between the corner tabs of adhesive tape 20 and extending the length of the terminal edge 12 provides an avenue of escape for any moisture or off-gassing from the healing wound. Unexpectedly, the medical protective wraps of this invention substantially prevent water from infiltrating to the wound or injury site during bathing while allowing condensation to escape over an extended period of use. The snug fit of the protective wrap allows the entire surface area of the first wrapping of sheet 4 to be in contact with the limb, thereby providing occlusion of the wound and a moist environment for the wound to heal. Also, the wrap prevents any slippage over extended use because the sheet snugly adheres to the limb across the entire surface area of the limb. In the process of applying the wrap, sheet 4 is pulled and extended around the body part allowing the interior of sheet 4 to stretch and form fit to the body part. However, because the sealing cuffs provide very little to almost no stretching, they merely form a reinforced band around the body part above and below the wound site.

After sheet 4 circumvents the limb 19 once and adheres to fasteners 20 on the bottom side 3 of the first terminal edge, sheet 4 is further stretched and wrapped upon itself and around the limb until the second terminal edge 14 with a strip of waterproof adhesive tape can be secured onto sheet 4 thereby providing little or no unnecessary looseness in the fit of the wrap. In the process of winding and stretching the protective wrap around a limb, a secure watertight fit is insured but not so constricting as to cause numbness in the limb over an extended period of time. The adhesive strip 18 extending the length of the second terminal edge 14 provides a sufficiently watertight seal to prevent infiltration of liquid to the wound site on the second terminal edge 14 while the sealing cuff 16 provides a sufficiently watertight fit to prevent infiltration of liquid to the wound site on the peripheral edges 6 and 8 of sheet 4.

In using the medical protective wrap of this invention, it may be beneficial for the healing process to administer to the wound site either hot or cold therapy techniques, such as subjecting a wound to a cold pack. If the temperature of the cold pack is near freezing than damage to skin tissue at the wound site is possible. Accordingly, it is envisioned by the inventor to fasten to sheet 4 an insulating packet 32 (shown in FIG. 1) positioned on the wound site in the interior or exterior of the applied medical wrap. The insulating packet may be any shape and fabricated from the same polymeric material as that of the medical wrap. The packet may be sealed on all peripheral edges having an insert of insulating material sealed therein. The insulating material may include cellulose materials, insulating polymers, glass fibers and the like, in the form of a blanket, foam, loose fill, and the like. The size of the insulating packet should be of a sufficient size to cover the wound site, and therefore, may require several different sizes to accomodate the specific body part. The insulating pack 32 may be fastened to sheet 4 by any medical adhesive known in the art, including pressure sensitive adhesives, such as rubber-based, acrylic, vinyl ether and hydrocolloid pressure sensitive adhesives.

Figure 10:
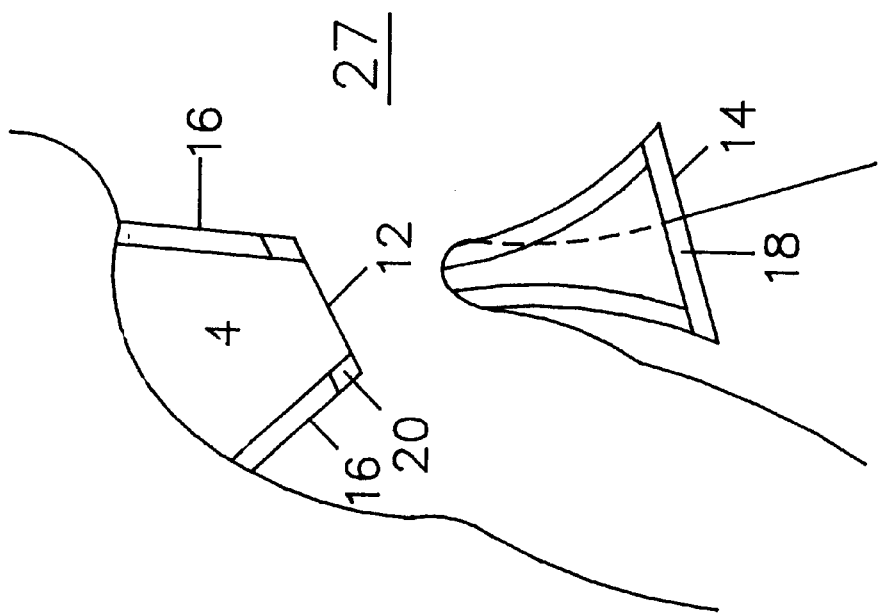
FIGS. 9 and 10 show modified embodiments of the medical protective wrap.
Figure 9:
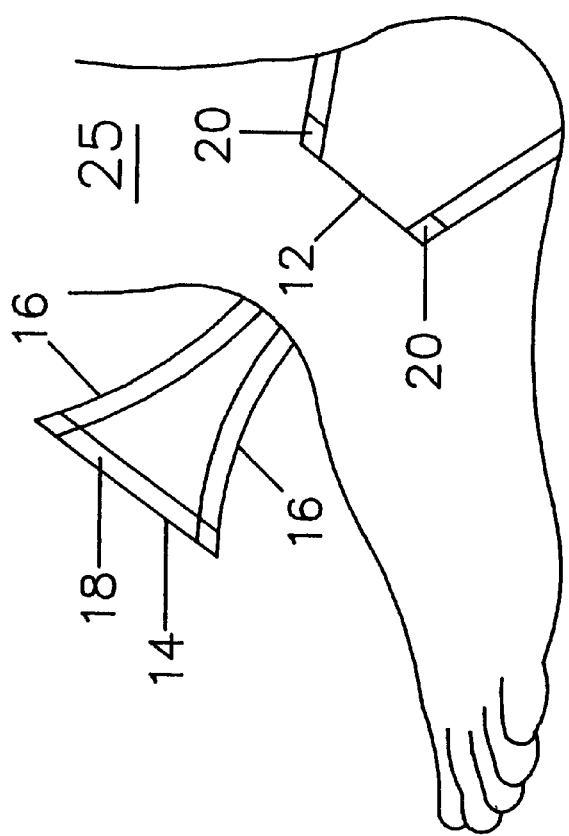

FIGS. 9 and 10 illustrate other sheet configurations of the medical protective wrap for use on a shoulder or heel injury. FIG. 10 shows the medical protective wrap 10 adapted for a shoulder 27. The means for fastening 20 on terminal edge 12 adheres to shoulder 27. Sheet 4 is stretched under the arm, around the circumference of the shoulder and fastened with means for fastening 18 which can be a strip of waterproof adhesive tape. The sealing cuff 16 forms a watertight seal on the first and second peripheral edge 6 and 8. This medical wrap may allow a patient, with recent shoulder surgery, to commence whirlpool therapy sooner after surgery while offering a waterproof barrier for the surgical incision.

FIG. 9 is a further adaption of the medical protective wrap 10 for a heel 25 with a similar wrapping around the heel and across the instep of the foot. These structural configurations of the medical protective wraps are merely representative of the different possibilities for use by patients. The structural configurations can vary and include but are not limited to rectangular, square, butterfly or any other configuration for elbow, chest, shoulder, etc.

While the invention has been described in conjunction with a specific embodiment thereof, it is evident that many alternatives, modifications and variations will be apparent to those skilled in the art in light of the foregoing detailed description.

I claim:

1. A medical protective wrap for a wound on a body part, which comprises:

a) a sheet of liquid impermeable, stretchable, flexible polymeric film of a sufficient dimension to wrap around the body part at least once;

b) first and second peripheral edges on opposing ends of the sheet;

c) a sealing cuff extending along said first and second peripheral edges, said sealing cuff having reduced stretchability relative to said sheet, and adapted for flush engagement with said body part;

d) a first and second terminal edge on said sheet running transverse to the longitudinal axis of said first and second peripheral edges;

e) at least one means for fastening onto the body on the first terminal edge; and f) at least one means for fastening onto the sheet on the second terminal edge.

2. The medical protective wrap of claim 1 wherein the polymeric film is a member selected from the group consisting of polyethylene, polypropylene, poly(vinyl chloride), polystyrene, polyurethane, poly(hexamethylene adipamide) and polysiloxane.

3. The medical protective wrap of claim 2 wherein the polymeric film comprises an embossed pattern.

4. The medical protective wrap of claim 1 wherein the polymeric film has a thickness range from about 1 to about 10 mil.

5. The medical protective wrap of claim 1 wherein the sealing cuff comprises a double faced adhesive strip sealed within at least one folding of the sheet onto itself running along substantially the entire length of the first and second peripheral edges.

6. The medical protective wrap of claim 5 wherein the sealing cuff is from about 1.5 to about 6.5 cm in width.

7. The medical protective wrap of claim 1 wherein the means for fastening on the first terminal edge is on two sides of the first terminal edge.

8. The medical protective wrap of claim 7 wherein the means for fastening on two sides of the first terminal edge comprises four (4) corner tabs of hypo-allergenic adhesive tape on opposite ends of the first terminal edge.

9. The medical protective wrap of claim 8 wherein the means for fastening on at least one side of the second terminal edge comprises a waterproof adhesive strip.

10. The medical protective wrap of claim 7 wherein the means for fastening on the top and bottom side of the first terminal edge comprises a strip of hypo-allergenic adhesive tape for folding over the first terminal edge.

11. The medical protective wrap of claim 10 wherein the means for fastening on the top side of the first terminal edge is available for fastening to the body part and the means for fastening on the bottom side of the first terminal edge is available for fastening to the sheet.

12. The medical protective wrap of claim 1 wherein the sealing cuff comprises a single faced adhesive strip attached directly to the sheet along the first and second peripheral edges, wherein the tacky side of said single adhesive strip adheres to the sheet.

13. The medical protective wrap of claim 1 wherein the sealing cuff comprises at least one folding of the sheet onto itself along the length of the first and second peripheral edges.

14. The medical protective wrap of claim 1 which is adapted for wrapping a body part selected from the group consisting of arm, leg, shoulder, torso, finger, foot and heel.

15. The medical protective wrap of claim 1 wherein the sheet adheres to the body part.

16. The medical protective wrap of claim 1 further comprising an antimicrobial agent.

17. The medical protective wrap of claim 16 wherein the antimicrobial agent is 2,4,4'-trichloro-2'-hydroxydiphenyl ether.

18. The medical protective wrap of claim 16 fabricated with a polymeric film impregnated with an antimicrobial agent.

19. The medical protective wrap of claim 1 wherein the liquid impermeable, stretchable, flexible polymeric film is further characterized by being moisture vapor permeable.

20. The medical protective wrap of claim 1 wherein the sheet further comprises an insulating packet positioned near the wound site.

21. A medical protective wrap for a wound on a body part, which comprises:

a) a sheet of liquid impermeable, stretchable, flexible polymeric film of a sufficient dimension to wrap around the body part at least once;

b) first and second peripheral edges on opposing ends of the sheet;

c) a sealing cuff extending along said first and second peripheral edges adapted for flush engagement with said body part comprising a v-shaped strip secured to the sheet along the first and second peripheral edges, wherein the apex of said v-shaped strip extends inwardly towards the interior of the wrap and each other;

d) a first and second terminal edge on said sheet running transverse to the longitudinal axis of said first and second peripheral edges;

e) at least one means for fastening onto the body on the first terminal edge; and f) at least one means for fastening onto the sheet on the second terminal edge.

22. A method for applying a medical protective wrap to protect a wound on a body part, the medical protective wrap comprising a liquid impermeable, stretchable polymeric sheet of a sufficient length to wrap around said body part at least once, sealing cuffs along opposing first and second peripheral edges of said sheet, said sealing cuff having reduced stretchability relative to said sheet, and adapted for flush engagement with said body part, first and second terminal edges running transverse to the longitudinal axis of said first and second peripheral edges, means for fastening to said body part on a top side of said first terminal edge and means for fastening to the sheet on a bottom side of the first terminal edge, and means for fastening the second terminal edge to said sheet, said method comprising the steps of:

a) applying to the body part the means for fastening on the top side of said first terminal edge of said sheet;

b) stretching and wrapping the sheet snugly around the wound on the body part at least once and to cause the sheet to adhere to the means for fastening on the bottom side of the first terminal edge wherein the body part is in contact with the sheet and the sealing cuffs in flush engagement with the tissue of the body; and c) fastening the second terminal edge to the sheet.

* * * * *